(12) United States Patent
Zhao et al.

(10) Patent No.: US 10,968,330 B2
(45) Date of Patent: Apr. 6, 2021

(54) PARTICULATE NUCLEATING AGENT AND METHOD FOR MANUFACTURING THE SAME

(71) Applicant: GCH Technology Co., Ltd., Guangzhou (CN)

(72) Inventors: Wenlin Zhao, Guangzhou (CN); Fangwen Guan, Guangzhou (CN)

(73) Assignee: GCH Technology Co., Ltd., Guangzhou (CN)

( * ) Notice: Subject to any disclaimer, the term of this patent is extended or adjusted under 35 U.S.C. 154(b) by 362 days.

(21) Appl. No.: 15/761,771

(22) PCT Filed: Dec. 20, 2016

(86) PCT No.: PCT/CN2016/110985
§ 371 (c)(1),
(2) Date: Mar. 20, 2018

(87) PCT Pub. No.: WO2018/112731
PCT Pub. Date: Jun. 28, 2018

(65) Prior Publication Data
US 2020/0131331 A1    Apr. 30, 2020

(51) Int. Cl.
*C08K 5/00* (2006.01)
*B01J 2/28* (2006.01)
*C08K 5/1575* (2006.01)

(52) U.S. Cl.
CPC ............... *C08K 5/0083* (2013.01); *B01J 2/28* (2013.01); *C08K 5/1575* (2013.01); *C08K 2201/003* (2013.01)

(58) Field of Classification Search
None
See application file for complete search history.

(56) References Cited

U.S. PATENT DOCUMENTS

| 4,902,807 A | 2/1990 | Kobayashi |
| 6,245,843 B1 | 6/2001 | Kobayashi et al. |
| 2003/0109610 A1 | 6/2003 | Nomoto |
| 2003/0193041 A1* | 10/2003 | Semen ............... B29B 9/12 252/400.24 |

FOREIGN PATENT DOCUMENTS

| CN | 1130617 A | 9/1996 |
| CN | 1241190 A1 | 1/2000 |
| CN | 1500120 A1 | 5/2004 |
| CN | 102675331 A | 9/2012 |
| KR | 20030049512 A | 6/2003 |
| WO | 2008012465 A2 | 1/2008 |

OTHER PUBLICATIONS

CN102675331A, Machine Translation, Sep. 19, 2012.
CN102675331A, English Translation of Abstract, Sep. 19, 2012.
WO 2008/012465A2, Machine Translation of the Description, Jan. 31, 2008.
CN1130617A, Machine Translation, Sep. 11, 1996.
KR20030049512A, Machine Translation, Jun. 25, 2003.
KR20030049512A, English Translation of the Abstract, Jun. 25, 2003.
International Search Report of PCT/CN2016/110985, dated Aug. 24, 2017.
Written Opinion of PCT/CN2016/110985, dated Aug. 24, 2017.

* cited by examiner

*Primary Examiner* — Robert T Butcher

(57) ABSTRACT

The present invention provides a particulate nucleating agent and a method for manufacturing the same. The particulate nucleating agent has an average radial crushing strength of 0.2-25.0N/cm. A weight content of the active ingredients in the particulate nucleating agent is no less than 90 wt %. The particulate nucleating agent is a transparent particulate nucleating agent. The particulate nucleating agent of the present invention can be fed smoothly during production without the change of the chemical composition thereof, so as to realize uniform dispersion in the polymer and reduce defects such as white dots in the polymer. The present invention breaks the traditional view of refining particles of nucleating agent to obtain a polymer having desirable properties, and avoids adding large amount of materials except the active ingredients during the granulation process of the nucleating agent.

18 Claims, No Drawings

# PARTICULATE NUCLEATING AGENT AND METHOD FOR MANUFACTURING THE SAME

CROSS REFERENCE TO RELATED APPLICATION

The present application is a U.S. national phase of international application, No. PCT/CN2016/110985, filed on Dec. 20, 2016, the disclosures of which are hereby incorporated by reference.

FIELD OF THE INVENTION

The present invention generally relates to nucleating agents for use in production of polymers and, more particularly, relates to a particulate nucleating agent and method for manufacturing the same, and a method for manufacturing polymers using the particulate nucleating agent.

BACKGROUND OF THE INVENTION

In production, nucleating agents are added into polymers. However, the powdery nucleating agent has fine granularity, small bulk density and static electricity. During the feeding process, the powdery nucleating agent is apt to adhere to a pipe, which may potentially lead to bridges and block, and further lead to uneven dispersion of the powdery nucleating agent in production and affect product quality of the polymer. In the prior art, one way to overcome this disadvantage is adding additives or antistatic agents which can improve fluidity into the nucleating agent, so as to improve the fluidity and the antistatic property of the nucleating agent. For instance, according to the disclosure of the prior art, ultrafine silica is added into 3988i of MILLKEN or stearic acid monoester (GMS) is added into 3988i of MILLKEN by other manufacturers. The foregoing method can remarkably improve the fluidity of the nucleating agent in the feeding process. However, the foregoing method cannot achieve uniformity of the feeding and reduce the purity of the product. Another way to overcome this disadvantage is to provide a premix which contains 50% active ingredients of nucleating agent via mixing antioxidant and acid scavenger in the formula, so as to achieve uniformity of feeding. However, this method limits the application flexibility of the formula and cannot achieve the diversity of products.

If the size of the particles of the nucleating agent is too small, i.e. powdery nucleating agent, dust is apt to occur, which may reduce the bulk density of the product and adversely affect the fluidity. The powder of the nucleating agent may form retention bridges in the feed hopper. If the size of the particles of the nucleating agent is too big, the nucleating agent is difficult to be dispersed evenly in the polymer, which may lead to uneven performances and quality instability of the polymer.

CN1500120 discloses a particulate or powdery diacetal composition including (A) at least one diacetal, (B) at least one anionic surfactant, and (C) at least one aliphatic monocarboxylic acid which may have at least one hydroxyl group in the molecule, wherein components (B) and (C) are uniformly dispersed in the particles of the particulate or powdery diacetal composition, and the weight content of component (B) in the diacetal composition is 0.1 to 3 weight % ("wt %") and the weight content of component (C) in the diacetal composition is 0.3-5 wt %, and the total weight content of components (B) and (C) in the diacetal composition is no more than 7 wt %. The composition may have any proper form and generally has a form of powder or particle, for instance having a shape of particle, cylinder and small spherical. As far as the form of powder is concerned, the average particle diameter thereof is 3-2000 μm, preferably 7-250 μm. If the average particle diameter is less than 3 μm, the property of the powder becomes poor and special crushing machinery is needed. As far as the form of particle is concerned, powdery diacetal composition can be formed into particulate diacetal composition having desirable shape and size. Compared with powdery diacetal composition, particulate diacetal composition can reduce dust and improve the fluidity of the particles. The particulate diacetal composition has a shape of particles, such as small particles or small round particles, and has desirable solubility and dispersibility in molten resin and various kinds of liquids. In addition, the particulate diacetal composition has desirable powder characteristics, such as better dust fluidity, less dust generated, less dust explosion and less adhesion to the inner wall of the feed hopper. CN1500120 intends to reduce dust and improve the fluidity of the particles via adding surfactant and controls the diameter of the particles. However, CN1500120 intends to reduce the melting point of the diacetal via adding specific anionic surfactants and specific aliphatic monocarboxylic acid.

CN1241190 discloses a particulate or powdery diacetal composition, comprising (a) at least one diacetal; and (b) at least one binder selecting from a group consisting of neutral or weakly acidic monovalent organic acid, neutral or weakly acidic polycarboxylic acid, certain salts of the neutral or weakly acidic polycarboxylic acid, sulfate, sulfonate, phosphate, organic phosphate, aluminum salt of neutral or weakly acidic polycarboxylic acid. The binder disperses evenly in the particles of the particulate or powdery diacetal composition. In the diacetal composition, the weight ratio of the binder to the diacetal is 0.01-100 to 100. The particle has a cylinder shape having a sectional diameter of 0.2-5 mm and a length of 0.2-15 mm. The particle can also have a shape of grain or disc having a diameter of 0.2-5 mm and a bulk density of 0.2-1.1 g/cm$^3$. CN1241190 can remarkably reduce the melting point of the diacetal. Via evenly dispersing the specific compound in the powder of diacetal, the diacetal composition obtained has improved solubility, dispersion and dissolution rate in molten resin and other fluids, and the improvement has nothing to do with the shape of the composition. The adhesive effect of the specific compound (i.e. promoting particle agglomeration or caking) can improve the bulk density of the diacetal composition to a level of no less than 0.2 g/cm$^3$, which can improve the fluidity and transportability of the diacetal powder, as well as inhibit the generation of the dust and adhesion of the diacetal on the wall of the equipments, for instance the pipe or the storage bucket. When the diacetal composition is used to form polyolefin resin pellets, the inherent nucleation property of the diacetal composition will be exhibited readily. Due to the sublimation of the nucleating agent, the extrusion die or the molding article will not be polluted. Generally, if the density of the diacetal composition increases remarkably, the fluidity of the powder increases while the dissolution rate is reduced. Conversely, if the density of the diacetal composition reduces remarkably, the dissolution rate of the powder increases while the fluidity is reduced. CN1241190 can remarkably reduce the melting point of the diacetal composition, because the increase of the density of the diacetal composition can improve the fluidity of the powder and the addition of the binder can improve the dissolution rate.

At present, there is still no technical solution which can successfully solve the problem of the fluidity and purity of the transparent nucleating agent. In some cases, the fluidity is increased at the cost of a reduced purity. In some other cases, the purity is increased at the cost of a reduced fluidity.

Generally, the fluidity is inversely proportional to the purity of the nucleating agent. The nucleating agent having desirable fluidity generally has low purity. The nucleating agent having high purity generally has poor fluidity.

The technical solution of the present invention can provide a solution to provide a desirable fluidity without affecting or slightly affecting the active ingredients of the nucleating agent, which can solve the problem of fluidity of the nucleating agent during preparation of polymer as well as provide desirable performances for the polymer prepared.

BRIEF SUMMARY OF VARIOUS EMBODIMENTS OF THE INVENTION

The present invention is aimed at manufacture of particulate nucleating agent via wet granulation method, which not only can solve the problems of fluidity of feeding and uniformity of polymer, but also can solve the problem of static electricity and dust. The particulate nucleating agent obtained via the method of the present invention has the same purity as that of the powdery nucleating agent, or has a purity of 2% less than that of the powdery nucleating agent, which is quite different from adding flow enhancers into transparent nucleating agent in the prior art.

One embodiment of the present invention provides a particulate nucleating agent comprising active ingredients in a weight content of no less than 90 weight % ("wt %") and having an average radial crushing strength of 0.2-25.0 N/cm.

According to one of the aspects of the present invention, the particulate nucleating agent is a transparent nucleating agent having an average radial crushing strength of 1.0-15.0 N/cm and active ingredients in a weight content of no less than 95 wt %.

According to one of the aspects of the present invention, a bulk density of the particulate nucleating agent is 0.25-0.60 g/cm$^3$ and an average volume of particles of the particulate nucleating agent is 0.5-200 mm$^3$.

According to one of the aspects of the present invention, the particulate nucleating agent includes large size particles, middle size particles and powdery particles, the middle size particle is particle which has average volume of 0.5-200 mm$^3$, i.e. the particle of average volume of 0.5-200 mm$^3$ is defined as the middle size particle, A particle having a volume greater than the volume of the middle size particles is defined as large size particles. A particle having a volume smaller than the volume of the middle size particle is defined as powdery particle. A weight content of the middle size nucleating agent particles in the particulate nucleating agent is no less than 70 wt %, and preferably no less than 80 wt %. Preferably, a weight content of the large size particle nucleating agent and the powdery particle nucleating agent in the total particulate nucleating agent is less than 30 wt %, and preferably less than 20 wt %. The weight ratio of the large size particle nucleating agent to the powdery particle nucleating agent is 1:0.1-10. Preferably, the particle of the particulate nucleating agent has a shape of cylinder, cone, frustum, sphere or ellipsoid. Preferably, the particle of the particulate nucleating agent has a shape of cylinder. The average radius of the cylinder is 0.25-3.5 mm, and preferably 0.50-2.5 mm, and an average length of the cylinder is 1-12 mm.

According to one of the aspects of the present invention, the active ingredients of the particulate nucleating agent include a single chemical composition, and the weight content of the single chemical composition in the particulate nucleating agent is no less than 96 wt %, and preferably no less than 98 wt %.

According to one of the aspects of the present invention, the active ingredients of the particulate nucleating agent include two transparent nucleating agents and the total weight content of the two transparent nucleating agents in the particulate nucleating agent is no less than 96 wt %, and preferably no less than 98 wt %.

According to one of the aspects of the present invention, the particulate transparent nucleating agent is sorbitol transparent nucleating agent. Preferably, the sorbitol transparent nucleating agent is 1,3:2,4-bis(p-chlorobenzylidene)-D-sorbitol, 1,3:2,4-bis(p-methylbenzyldene)-D-sorbitol, 1,3:2,4-bis(3,4-dimethylbenzylidene)-D-sorbitol or 1,3:2,4-bis(4'-propylbenzylidene)-1-propyl sorbitol, or the particulate transparent nucleating agent is a mixture of 1,3:2,4-bis(p-chlorobenzylidene)-D-sorbitol and 1,3:2,4-bis(3,4-dimethylbenzylidene)-D-sorbitol.

According to another embodiment of the present invention, a polymer manufactured via using the particulate transparent nucleating agent in accordance with the present invention is provided, wherein a weight content of the particulate transparent nucleating agent added in the polymer in manufacturing process is 1-4 wt %.

According to yet another embodiment of the present invention, a method for manufacturing a polymer having uniform properties via using the particulate nucleating agent of the present invention is provided, wherein 1-4 wt % of the particulate nucleating agent of the present invention is added in the polymer resin during a manufacturing process of the polymer.

According to still another embodiment of the present invention, a polymer article manufactured via using the particulate nucleating agent of the present invention is provided.

According to a further embodiment of the present invention, a method for manufacturing the particulate nucleating agent of the present invention is provided. The method includes the steps of: providing powdery nucleating agent comprising active ingredients, adding 0.25-4 parts by weight of water into 1 part by weight of powdery nucleating agent and stirring to obtain a mixture; extruding the mixture at an extrusion pressure of 0.5-7.0 Mpa and adjusting a ratio of the water content in the powdery nucleating agent to the extrusion pressure to 0.15-0.40; and drying the extruded particles to obtain the particulate nucleating agent. Preferably, a binder is added into the water, and a weight content of the binder in the mixture of the water and the powdery nucleating agent is 0.01-2.00 wt %. Preferably, the binder is water-soluble straight-chain polymer.

In order to provide desirable fluidity of transparent nucleating agents, application convenience of transparent nucleating agents as well as application performances of transparent nucleating agents in polymers, one of the aspects of the present invention forms a transparent nucleating agent of the present invention into particles, or adds small amount of binder into the transparent nucleating agent. The particulate nucleating agent obtained not only has desirable fluidity, but also can improve the performances of the polymer. The present invention breaks the traditional view of refining particles of nucleating agent to obtain polymer having desirable performances.

During the manufacturing process of the high purity particulate nucleating agent of the present invention, there is no need to add additive or only need to add small amount of binder. In this case, particles of the transparent nucleating agent inherit the inherent properties of the high purity transparent nucleating agent. The particulate nucleating agent can be readily added in the manufacturing process. There is no need to increase the added weight of the particulate nucleating agent. The polymer manufactured has improved performances. Especially for the particulate transparent nucleating agent, if the average radial crushing strength of the particulate transparent nucleating agent is 1.0-15 N/cm, the polymer prepared from the particulate transparent nucleating agent has better transparency than that of a polymer prepared from powdery transparent nucleating agent of the prior art. In addition, there is no uneven transparency in the polymer prepared via using the particulate transparent nucleating agent of the present invention.

In order to ensure the transparent particulate nucleating agent obtained can meet the requirements of average radial crushing strength, in-depth study has been carried out on the extrusion process, so as to obtain the relationship between the water content in the powder and the extrusion pressure during extrusion process and obtain optimum granulation conditions to obtain optimum average radial crushing strength.

Other advantages and novel features will be drawn from the following detailed description of preferred embodiments. The detailed description of the embodiments given below serves to explain the principles of the invention:

DETAILED DESCRIPTION OF THE INVENTION

Example embodiments of the present invention will now be described more fully hereinafter. Indeed, the invention may be embodied in many different forms and should not be construed as limited to the embodiments set forth herein; rather, these embodiments are provided so that this disclosure will satisfy applicable legal requirements.

Definition of Terms

Active ingredients in the present invention refer to ingredients which can affect the properties of the polymer directly, for instance, sorbitol transparent nucleating agent which can improve the transparency of the polymer, i.e. 1,3:2,4-bis(p-chlorobenzylidene)-D-sorbitol, 1,3:2,4-bis(p-methylbenzylidene)-D-sorbitol, 1,3:2,4-bis(3,4-dimethybenzylidene)-D-sorbitol or 1,3:2,4-bis(4'-propylbenzylidene)-1-propyl sorbitol, are all active ingredients. Other additives for stability of the active ingredients, easy transport and easy application are not active ingredients in the present invention.

For transparent nucleating agent, content of active ingredient of the transparent nucleating agent refers to the purity of the nucleating agent. For instance, when the content of the active ingredient in the transparent nucleating agent is 98%, the purity of the transparent nucleating agent is 98%.

As an example of the nucleating agent of the present invention, 5000 g transparent nucleating agent having a purity of higher than 95% is added into 1250-10000 g water. Cylinder particles are obtained in an extrusion granulator. The extrusion pressure is adjusted. The ratio of the water content of the powder and the extrusion pressure is adjusted, to adjust the particle density. The obtained particles are dried to obtain the particulate transparent nucleating agent product. The following particulate transparent nucleating particles can be obtained via the method of the present invention.

Particle A: 1,3:2,4-bis(p-methyl benzylidene) sorbitol

Particle B: 1,3:2,4-bis(3,4-dimethyl benzylidene)-1)-sorbitol

Particle C: 1,3;2,4-bis(4'-propylbenzylidene)-1-propyl sorbitol

Method for Testing the Volume of the Particles (Sieve Analysis Method)

A sieve tray having an aperture of 3.5 mm and a chassis having an aperture of 0.25 mm are stacked up in order to obtain three layers of sieve trays. A 100 g sample (m) is added into the top sieve tray having an aperture of 3.5 mm and the top sieve tray is covered with a cap. The sieve is held in hand and shaken for 3~5 min. The cap is then opened and the top sieve is removed to obtain the material on the sieve. The weight of the material on the sieve is tested and indicated as the weight of the large size particles ($m_{large\ size}$).

The forgoing operation is repeated. After the sieve in each layer is shaken for the same time, the sample on the chassis is removed and weighted, to obtain the weight of the small size particles ($m_{small\ size}$). The operation is repeated for three times to obtain an average value. The content of the middle size particles is calculated according to the formula as following:

the content of the middle size particles=(100−($m_{large\ size}$+$m_{small\ size}$))/100.

Method for Testing Bulk Density of the Particles

Method for testing the bulk density includes the steps of: at a temperature of 20° C. and a humidity of 60%, dropping a 200 ml measuring cylinder having a diameter of 38 mm and 35 g samples received therein from a height of 10~20 mm to a rubber cushion for 50 times; testing the volume of the samples in the measuring cylinder and calculating the bulk density; and repeating the foregoing steps for three times and obtaining an average value as the bulk density.

Fluidity Test 30 g sample is added into a repose angle measuring instrument (GB11986-89) slowly via an upper funnel. The material flows out from a bottom of the funnel forms a tilt angle of a conical accumulation body on a horizontal plane. The height h and the diameter R of the conical accumulation body are measured respectively. The repose angle is calculated according to a formula, $$\varphi = \arctan\frac{2h}{R}.$$

The repose angle calculated acts as an index of the fluidity. The smaller the repose angle is, the higher the fluidity is.

Dispersion Test 1000 parts by weight of homopolymer polypropylene resin, 2 or 1 parts by weight of nucleating agent powder or particles are dry mixed in a Henschel mixer. The mixture obtained is extruded in a twin-screw extruder at 210° C. to obtain a stripe. The stripe obtained is cooled via water and then cut into particles. The particles are injection molded at a resin temperature of 230° C. and a molding temperature of 60° C., to obtain a square sample of 60 mm×60 mm having a thickness of 1 mm. The number of spots due to the nucleating agent composition fails to disperse in the test stripe is tested and the haze of the stripe is tested. Blank samples are used as comparative samples.

Method for Testing Hardness

A KQ-3type automatic particle strength tester having a range of 0-150 mm and a sensitivity of 12.34 is used to test the hardness. Two ends of each sample to be tested are polished via zero sandpaper. After testing the length of the particles via calipers, each sample is set in a center of a test table and tested according to the regulations of the instrument. 40-100 particles of a same sample are tested and the average value is taken. Radial crushing strength of an individual single sample is calculated according to formula $$P_i 径 = \frac{F_i}{L},$$

wherein $P_i$ 径 is the radial crushing strength of an individual sample (N/cm), $F_i$ is the crushing force of an individual sample (N), and L is the length of the single sample (cm).

Haze test is carried out according to ASTM D1003.

EXAMPLES

Embodiment 1

1. Preparation of Particles of the Transparent Nucleating Agent and Preparation of Polymer Via Using the Particles of the Transparent Nucleating Agent

1. Preparation of Particles of the Transparent Nucleating Agent

One part by weight of 1,3:2,4-bis(p-methyl benzylidene)-D-sorbitol having a purity of 98% was wetted by 0:25-2 parts by weight of water. The wetted nucleating agent was extruded at different pressures to obtain wetted particles respectively. The wetted particles were dried. The bulk density and the portion of the middle size particles of the nucleating agent were tested to obtain transparent nucleating agent particle A1, A2, A3, A4, A5, A6, A7, A8, A9, A10, A11, A12, A13, A14. At the same time, powder of the nucleating agent 1,3:2,4-bis(p-methylbenzylidene)-D-sorbitol was used as comparative sample A15.

One part by weight of 1,3:2,4-bis(3,4-benzylidene)-D-sorbitol having a purity of 98% was wetted by 0.25-2 parts by weight of water. The wetted nucleating agent was extruded at different pressures, so as to obtain wetted particles respectively. The wetted particles were dried. The bulk density and the portion of the middle size particles of the nucleating agent were tested to obtain transparent nucleating agent particle B1, B2, B3, B4, B5, B6, B7, B8, B9, B10, B11, B12, B13, B14. At the same time, powder of the nucleating agent 1,3:2,4-bis(3,4-dimethylbenzylidene)-D-sorbitol was used as comparative sample B15.

One part by weight of 1,3;2,4-bis(4'-propylbenzylidene)-1-propyl sorbitol having a purity of 98% was wetted by 0.25-2 parts by weight of water. The wetted nucleating agent was extruded at different pressures, so as to obtain wetted particles respectively. The wetted particles were dried. The bulk density and the portion of the middle size particles of the nucleating agent were tested to obtain transparent nucleating agent particle C1, C2, C3, C4, C5, C6, C7, C8, C9, C10, C11, C12, C13, C14. At same time, powder of the nucleating agent 1,3;2,4-bis(4'-propylbenzylidene)-1-propyl sorbitol was used as comparative sample C15.

TABLE 1

Property parameters of particulate transparent nucleating agent and property parameters of comparative powdery transparent nucleating agent

| Nucleating agent | Before manufacturing Bulk density g/cm³ | After manufacturing Bulk density g/cm3 | After manufacturing Portion of middle size particles (% wt) | After manufacturing Average radial crushing strength (N/cm) | Fluidity |
|---|---|---|---|---|---|
| Particle A1 | 0.18 | 0.22 | 55.6 | 0.13 | Bad |
| Particle A2 | 0.20 | 0.23 | 71.8 | 0.22 | Slightly worse |
| Particle A3 | 0.17 | 0.24 | 75.5 | 0.56 | Slightly worse |
| Particle A4 | 0.18 | 0.26 | 79.3 | 0.82 | Slightly worse |
| Particle A5 | 0.0 | 0.34 | 85.5 | 1.95 | Good |
| Particle A6 | 0.19 | 0.36 | 88.2 | 3.64 | Good |
| Particle A7 | 0.20 | 0.37 | 90.4 | 5.18 | Good |
| Particle A8 | 0.18 | 0.39 | 90.8 | 9.52 | Good |
| Particle A9 | 0.19 | 0.45 | 91.5 | 12.32 | Good |
| Particle A10 | 0.18 | 0.48 | 92.3 | 14.20 | Good |
| Particle A11 | 0.18 | 0.51 | 93.8 | 19.55 | Good |
| Particle A12 | 0.19 | 0.52 | 94.5 | 22.10 | Good |
| Particle A13 | 0.20 | 0.55 | 94.9 | 24.41 | Good |
| Particle A14 | 0.18 | 0.57 | 95.6 | 27.31 | Good |
| Particle A15 | 0.19 | — | — | — | Bad |
| Particle B1 | 0.18 | 0.22 | 53.5 | 0.13 | Bad |
| Particle B2 | 0.20 | 0.24 | 0.69 | 0.21 | Slightly worse |
| Particle B3 | 0.20 | 0.25 | 71.4 | 0.56 | Slightly worse |
| Particle B4 | 0.21 | 0,27 | 76.8 | 0.74 | Slightly worse |
| Particle B5 | 0.20 | 0.34 | 82.3 | 1.64 | Good |
| Particle B6 | 0.18 | 0.36 | 85.6 | 3.87 | Good |
| Particle B7 | 0.20 | 0.38 | 88.6 | 5.65 | Good |
| Particle B8 | 0.19 | 0.42 | 90.2 | 8.96 | Good |

TABLE 1-continued

Property parameters of particulate transparent nucleating agent and property parameters of comparative powdery transparent nucleating agent

| Nucleating agent | Before manufacturing Bulk density g/cm³ | After manufacturing | | | |
|---|---|---|---|---|---|
| | | Bulk density g/cm3 | Portion of middle size particles (% wt) | Average radial crushing strength (N/cm) | Fluidity |
| Particle B9 | 0.18 | 0.46 | 91.5 | 11.22 | Good |
| Particle B10 | 0.20 | 0.48 | 92.0 | 14.85 | Good |
| Particle B11 | 0.18 | 0.53 | 93.6 | 19.05 | Good |
| 颗粒 B12 Particle B12 | 0.18 | 0.34 | 94.2 | 21.31 | Good |
| Particle B13 | 0.19 | 0.56 | 95.8 | 24.58 | Good |
| Particle B14 | 0.20 | 0.58 | 97.5 | 28.26 | Good |
| Powder B15 | 0.19 | — | — | — | Bad |
| Powder C1 | 0.29 | 0.28 | 55.6 | 0.17 | Bad |
| Powder C2 | 0.28 | 0.29 | 71.8 | 0.28 | Slightly worse |
| Powder C3 | 0.30 | 0.30 | 75.5 | 0.76 | Slightly worse |
| Powder C4 | 0.31 | 0,31 | 79.3 | 0.88 | Slightly worse |
| Powder C5 | 0.30 | 0.32 | 85.5 | 2.05 | Good |
| Powder C6 | 0.31 | 0.33 | 88.2 | 5.43 | Good |
| Powder C7 | 0.30 | 0,35 | 90.4 | 5.76 | Good |
| Powder C8 | 0.31 | 0.39 | 90.8 | 10.19 | Good |
| Powder C9 | 0.29 | 0.45 | 91.5 | 13.81 | Good |
| Powder C10 | 0.30 | 0.48 | 92.3 | 15.11 | Good |
| Powder C11 | 0.31 | 0.54 | 93.8 | 18.94 | Good |
| Powder C12 | 0.32 | 0.55 | 94.5 | 21.88 | Good |
| Powder C13 | 0.32 | 0.56 | 94.9 | 25.08 | Good |
| Powder C14 | 0.30 | 0.57 | 95.6 | 28.71 | Good |
| Powder C15 | 0.31 | — | — | — | Bad |

During the preparation of Particle A5, A6, A7, A8, A9, A10, A11, Particle B5, B6, B7, B8, B9, B10, B11, Particle C5, C6, C7, C8, C9, C10, C11, the ratio of the water content and the extrusion pressure is adjusted within the range of 0.15-0.40.

The fluidity extremely relates to the average radial crushing strength and portion of the middle size particles of the nucleating agent. When the crushing strength was too small (less than 0.2 N/cm), and portion of the middle size particles was low, the fluidity would become very poor. When the crushing strength was less than 1 N/cm, the fluidity is slightly worse. When the crushing strength increases gradually, portion of the middle size particles and the fluidity may increase accordingly.

2. Preparation of Polymer Using Transparent Nucleating Agent Particles

Particle A1, Particle A2, Particle A3, Particle A4, Particle A5, Particle A6, Particle A7, Particle A8, Particle A9, Powder A10, Particle A11, Particle A12, Particle A13, Particle A14, Powder A15, Particle B1, Particle B2, Particle B3, Particle B4, Particle B5, Particle B6, Particle B7, Particle B8, Particle B9, Powder B10, Particle B11, Particle B12 Particle B13, Particle B14, Powder B15, Particle C1, Particle C2, Particle C3, Particle C4, Particle C5, Particle C6, Particle C7, Particle C8, Particle C9, Particle C10, Particle C11, Particle C12, Particle C13, Particle C14, Powder C15 of the nucleating agent were added into polymer basic material respectively, to obtain the polymer, with the adding weight of each nucleating agent particle was 2% of the weight of the polymer. The haze, the white dot, the crystal point and the transparent evenness of the polymer were tested, wherein the basic material was homopolymer polypropylene having a MI of 10 g/10 min.

TABLE 2

Performances of polymer prepared via using particulate transparent nucleating agent and powdery transparent nucleating agent

| Nucleating agent | Properties of the polymer prepared via adding powdery nucleating, agent in the basic material of the polymer | | Properties of the polymer prepared via adding particulate nucleating agent in the basic material of the polymer | | |
|---|---|---|---|---|---|
| | Haze | White dot/Crystal point | Haze | White dot/Crystal point | Transparent evenness of the polymer |
| Particle A1 | 13.0 | No | 12.9 | No | Occasionally partially uneven |
| Particle A2 | 13.4 | No | 13.0 | No | Even |
| Particle A3 | 13.3 | No | 13.0 | No | Even |
| Particle A4 | 13.4 | No | 13.1 | No | Even |

TABLE 2-continued

Performances of polymer prepared via using particulate transparent nucleating agent and powdery transparent nucleating agent

| Nucleating agent | Properties of the polymer prepared via adding powdery nucleating agent in the basic material of the polymer | | Properties of the polymer prepared via adding particulate nucleating agent in the basic material of the polymer | | |
|---|---|---|---|---|---|
| | Haze | White dot/Crystal point | Haze | White dot/Crystal point | Transparent evenness of the polymer |
| Particle A5 | 13.2 | No | 13.0 | No | Even |
| Particle A6 | 13.3 | No | 13.1 | No | Even |
| Particle A7 | 13.3 | No | 13.2 | No | Even |
| Particle A8 | 13.4 | No | 13.2 | No | Even |
| Particle A9 | 13.1 | No | 13.1 | No | Even |
| Particle A10 | 13.2 | No | 13.0 | No | Even |
| Particle A11 | 13.2 | No | 13.2 | No | Partially uneven |
| Particle A12 | 13.3 | No | 13.2 | No | Partially uneven |
| Particle A13 | 13.4 | No | 13.3 | No | Partially uneven |
| Particle A14 | 13.2 | Yes | 14.3 | Yes | Partially uneven |
| Particle A15 | 13.2 | No | 13.1 | No | Partially uneven |
| ParticleB1 | 13.4 | No | 13.3 | No | Occasionally partially uneven |
| ParticleB2 | 13.2 | No | 13.1 | No | Even |
| ParticleB3 | 13.4 | No | 13.3 | No | Even |
| ParticleB4 | 13.0 | No | 13.0 | No | Even |
| ParticleB5 | 13.1 | No | 13.2 | No | Even |
| ParticleB6 | 13.2 | No | 13.2 | No | Even |
| ParticleB7 | 13.1 | No | 13.1 | No | Even |
| ParticleB8 | 13.3 | No | 13.2 | No | Even |
| ParticleB9 | 13.2 | No | 13.1 | No | Even |
| ParticleB10 | 13.3 | No | 13.0 | No | Even |
| ParticleB11 | 13.4 | No | 13.1 | No | Partially uneven |
| ParticleB12 | 13.4 | No | 13.2 | No | Partially uneven |
| ParticleB13 | 13.3 | No | 13.2 | No | Partially uneven |
| ParticleB14 | 13.2 | Yes | 14.2 | Yes | Partially uneven |
| Powder B15 | 13.4 | No | 13.1 | No | Partially uneven |
| Particle C1 | 14.1 | No | 14.2 | No | Occasionally partially uneven |
| Particle C2 | 14.2 | No | 14.1 | No | Even |
| Particle C3 | 14.1 | No | 14.2 | No | Even |
| Particle C4 | 14.3 | No | 14.3 | No | Even |
| Particle C5 | 14.2 | No | 14.1 | No | Even |
| Particle C6 | 14.3 | No | 14.2 | No | Even |
| Particle C7 | 14.2 | No | 14.3 | No | Even |
| Particle C8 | 14.1 | No | 14.1 | No | Even |
| Particle C9 | 14.1 | No | 14.2 | No | Even |
| Particle C10 | 14.3 | No | 14.1 | No | Even |
| Particle C11 | 14.1 | No | 14.2 | No | Partially uneven |
| Particle C12 | 14.2 | No | 14.8 | Yes | Partially uneven |
| Particle C13 | 14.2 | No | 15.1 | Yes | Partially uneven |
| Particle C14 | 14.3 | No | 15.6 | Yes | Partially uneven |
| Powder C15 | 14.2 | No | 13.9 | No | Partially uneven |

The transparent evenness of the polymer was determined via testing haze at various points of the polymer prepared according to multi-point crossover sampling principle. If the hazes of adjacent 1-5 sampling points were 5 higher than the lowest haze, it was indicated as occasionally partially uneven. If the hazes of more than 5 sampling points were 5 higher than the lowest haze, it was indicated as partially uneven. If the cases as mentioned above did not exist, it was indicated as even.

Testing results show that if the crushing strength was too big, for instance higher than 25 N/cm, the white dots increase and the haze were undesirable. If the crushing strength was higher than 15 N/cm, the polymer had a poor transparent evenness due to slow dispersion of the particles. Therefore, a crushing strength of less than 25 N/cm could meet the requirements on the performances of the polymer prepared. A crushing strength of less than 15 N/cm could avoid transparent unevenness of the polymer.

In preparation of the polymer, when the weight ratio of the retention nucleating agent generated to the total feeding nucleating agent was 0.5%, the polymer prepared had uniform performances.

In preparation of the transparent nucleating agent, via adjusting the amount of the water added and the pressure strength for extrusion granulation, particles having different average radial crushing strength could be obtained. During testing the effect of the particles at the performances of the polymer, it was found that an average radial crushing strength of 0.2-25.0 N/cm could meet the requirements of the fluidity in the preparation of the polymer and meet the requirements of basic requirements toward the performances of the polymer. When the average radial crushing strength of the particles was 1.0-15.0 N/cm, the desirable fluidity of the particles of the transparent nucleating agent during the preparation of the polymer could be ensured, and the transparent performance of the polymer could be improved, especially the transparent evenness of the polymer. Therefore, via forming the transparent nucleating agent into particles having specific strength, the application manner of the transparent nucleating agent could be optimized and the application effect of the transparent nucleating agent could be improved.

According to the method detailed above, the water content of the powder and the extrusion pressure during extrusion process are adjusted. When the ratio of the water content of the powder to the extrusion pressure is 0.15-0.40, particles which has desirable average radial crushing strength is obtained, so as to ensure the properties of the particles in the polymer.

Test of Adding Water-Soluble Straight-Chain Polymer into Water

In the preparation of the particles of the transparent nucleating agent, 0.01 wt %-2.00 wt % of water-soluble straight-chain polymer relative to the total weight of the transparent nucleating agent and water was added into the water. Testing results show that adding small amount of binder could play a certain role in improving the surface smoothness and hardness of the particles, because the small amount of the binder would not affect the purity of the transparent nucleating agent in the particles and would not affect the performances of the transparent nucleating agent in the polymer.

Consequently, small amount of binder, preferably water-soluble straight-chain polymer, can be added during preparation of the particulate nucleating agent. Via adding binder, crushing strength of the particulate nucleating agent can be improved. Therefore, during the manufacturing process, via adjusting the extrusion pressure, the crushing strength can also be adjusted, so as to meet the requirements of the product properties.

What is claimed is:

1. A particulate nucleating agent comprising active ingredients in a weight content of no less than 90 weight % and having an average radial crushing strength of 1.64-25.0 N/cm, wherein the particulate nucleating agent comprises large size nucleating agent particles having average volume greater than 200 mm$^3$, middle size nucleating agent particles having average volume of 0.5-200 mm$^3$ and powdery nucleating agent particles having average volume less than 0.5 mm$^3$, and a weight content of the middle size nucleating agent particles in the total particulate nucleating agent is no less than 82.3 weight %.

2. The particulate nucleating agent of claim 1, wherein the particulate nucleating agent is a transparent nucleating agent having an average radial crushing strength of 1.64-15.0 N/cm and active ingredients in a weight content of no less than 95 wt %.

3. The particulate nucleating agent of claim 1, wherein a bulk density of the particulate nucleating agent is 0.25-0.6 g/cm$^3$ and an average volume of particles in the particulate nucleating agent is 0.5-200 mm$^3$.

4. The particulate nucleating agent of claim 1, wherein a total weight content of the large size nucleating agent particles and the powdery nucleating agent particles in the particulate nucleating agent is less than 30 weight %, and a weight ratio of the large size nucleating agent particles to the powdery nucleating agent particles is 1:0.1-10.

5. The particulate nucleating agent of claim 1, wherein the particles of the particulate nucleating agent each has a shape of a column, cone, frustum, sphere or ellipsoid.

6. The particulate nucleating agent of claim 5, wherein the particles of the particulate nucleating agent each has a shape of a cylinder having an average radius of 0.25-3.5 mm, and an average length of 1-12 mm.

7. The particulate nucleating agent of claim 6, wherein the average radius of the cylinder is 0.50-2.5 mm.

8. The particulate nucleating agent of claim 1, wherein the active ingredients of the particulate nucleating agent comprise a single nucleating agent, and a weight content of the single nucleating agent in the particulate nucleating agent is no less than 96 weight %.

9. The particulate nucleating agent of claim 1, wherein the active ingredients of the particulate nucleating agent comprise two nucleating agents, and a total weight content of the two nucleating agents is no less than 96 weight %.

10. The particulate nucleating agent of claim 1, wherein the nucleating agent is transparent sorbitol nucleating agent.

11. The particulate nucleating agent of claim 10, wherein the transparent sorbitol nucleating agent is 1,3:2,4-bis(p-chlorobenzylidene)-D-sorbitol, 1,3:2,4-bis(p-methylbenzylidene)-D-sorbitol, 1,3:2,4-bis(3,4-dimethylbenzylidene)-D-sorbitol or 1,3:2,4-bis(4'-propylbenzylidene)-1-propyl sorbitol, or the sorbitol transparent nucleating agent is a mixture of 1,3:2,4-bis(p-chlorobenzylidene)-D-sorbitol and 1,3:2,4-bis(3,4-dimethylbenzylidene)-D-sorbitol.

12. A polymer manufactured using the particulate nucleating agent of claim 1, wherein the particulate nucleating agent is added in polymer in a weight content of 1-4 weight % during the manufacturing of the polymer.

13. A method for manufacturing a polymer having uniform performances using the particulate nucleating agent of claim 1, wherein 1-4 weight of the particulate nucleating agent of claim 1 is added in the polymer during the manufacturing of the polymer.

14. A method for manufacturing the particulate nucleating agent of claim 1, comprising the steps of: providing a powdery nucleating agent comprising the active ingredients; adding 0.25 to 4.0 parts by weight of water into 1 part by weight of powdery nucleating agent and stirring, and obtaining a mixture; extruding the mixture at an extrusion pressure of 0.5-7 Mpa and adjusting a ratio of the water content in the powdery nucleating agent to the extrusion pressure to 0.15-0.40; and drying the extruded particles and obtaining the particulate nucleating agent.

15. The method of claim 14, wherein a binder is also added into the water, and a weight content of the binder in the mixture of the water and the powdery nucleating agent is 0.01-2.00%.

16. The method of claim 14, wherein the binder is water-soluble straight-chain polymer.

17. The particulate nucleating agent of claim 1, wherein the active ingredients of the particulate nucleating agent comprise a single nucleating agent, and a weight content of the single nucleating agent in the particulate nucleating agent is no less than 98 weight %.

18. The particulate nucleating agent of claim 1, wherein the active ingredients of the particulate nucleating agent comprise two nucleating agents, and a total weight content of the two nucleating agents is no less than 98 weight %.

* * * * *